(12) United States Patent
Le Digabel et al.

(10) Patent No.: US 9,174,864 B2
(45) Date of Patent: Nov. 3, 2015

(54) BACTERIA OF THE GENUS PSEUDOXANTHOMONAS THAT ARE CAPABLE OF DEGRADING METHYL TERT-BUTYL ETHER (MTBE) INTO A SOLUTION IN EFFLUENT

(71) Applicant: IFP Energies nouvelles, Rueil-Malmaison Cedex (FR)

(72) Inventors: Yoann Le Digabel, Puteaux (FR); Francoise Fayolle-Guichard, Paris (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 16 days.

(21) Appl. No.: 13/947,162

(22) Filed: Jul. 22, 2013

(65) Prior Publication Data

US 2014/0027375 A1    Jan. 30, 2014

(30) Foreign Application Priority Data

Jul. 25, 2012    (FR) .................................... 12 02104

(51) Int. Cl.
| | |
|---|---|
| C02F 3/34 | (2006.01) |
| A62D 3/02 | (2007.01) |
| C12N 1/20 | (2006.01) |
| C12R 1/01 | (2006.01) |
| A62D 101/28 | (2007.01) |
| C02F 101/34 | (2006.01) |

(52) U.S. Cl.
CPC ... *C02F 3/34* (2013.01); *A62D 3/02* (2013.01); *C12N 1/20* (2013.01); *C12R 1/01* (2013.01); *A62D 2101/28* (2013.01); *C02F 2101/34* (2013.01)

(58) Field of Classification Search
None
See application file for complete search history.

(56) References Cited

FOREIGN PATENT DOCUMENTS

WO    00/63343 A2    10/2000

OTHER PUBLICATIONS

Hanson et al., App. Env. Microbiol. 65(11): 4788-4792 (1999).*
Search Report from FR1202104 dated Mar. 25, 2013.
Y. Le Digabel "Pseudoxanthomonas sp. IFP 2051 16S ribosomal RNA gene, partial sequence" Database Embl (Online), [Jan. 2013], 1 page.
M. Kharoune et al. "Isolation and characterization of two aerobic bacterial strains that completely degrade ethyl tert-butyl ether (ETBE)" Applied Microbiology and Biotechnology, vol. 55, No. 3, [Apr. 2001], pp. 348-353.
K. Mo et al. "Biodegradation of methyl t-butyl ether by pure bacterial cultures" Applied Microbiology and Biotechnology, vol. 47, [1997], pp. 69-72.
Robert J. Steffan et al. "Biodegradation of the Gasoline Oxygenates Methyl tert-Butyl Ether, Ethyl tert-Butyl Ether, and tert-Amyl Methyl Ether by Propane-Oxidizing Bacteria" Applied and Environmental Microbiology, vol. 63, No. 11, [Nov. 1997], pp. 4216-4222.
P. Piveteau et al. "Biodegradation of tert-butyl alcohol and related xenobiotics by a methylotrophic bacterial isolate" Applied Microbiology and Biotechnology, vol. 55, No. 3, [Apr. 2001], pp. 369-373.
Paul B. Hatzinger, et al. "Biodegradation of Methyl tert-Butyl Ether by a Pure Bacterial Culture" Applied and Environmental Microbiology, vol. 67, No. 12, [Dec. 2001], pp. 5601-5607.
Alan Francois et al. "Biodegradation of Methyl tert-Butyl Ether and Other Fuel Oxygenates by a New Strain, Mycobacterium austroafricanum IFP 2012" Applied and Environmental Microbiology, vol. 68, No. 6, [Jun. 2002], pp. 2754-2762.
Jessica R. Hanson et al. "Biodegradation of Methyl tert-Butyl Ether by a Bacterial Pure Culture" Applied and Environmental Microbiology, vol. 65, No. 11, [Nov. 1999], pp. 4788-4792.

* cited by examiner

*Primary Examiner* — Patricia A Leith
*Assistant Examiner* — Erin M Bowers
(74) *Attorney, Agent, or Firm* — Millen, White, Zelano & Branigan, P.C.

(57) ABSTRACT

This invention relates to bacteria of the genus *Pseudoxanthomonas* and in particular the strain deposited on Jul. 12, 2012 at the Pasteur Institute (CNCM, 25 rue du Docteur Roux, F-75724 PARIS Cedex 15, France) under No. CNCM I-4657, capable of degrading MTBE and/or TBA.
The invention also relates to a process for treatment of an effluent comprising MTBE and optionally TBA using such bacteria.

8 Claims, 1 Drawing Sheet

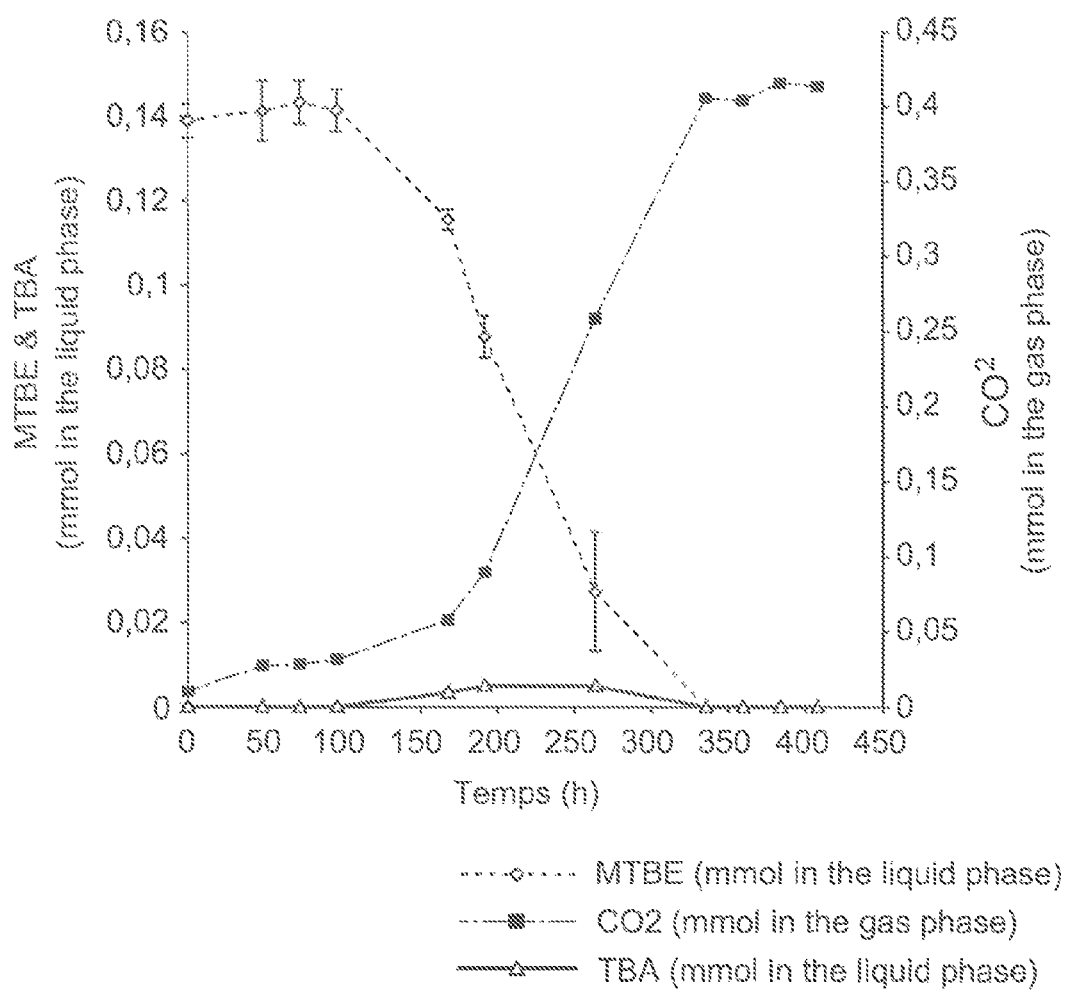

BACTERIA OF THE GENUS PSEUDOXANTHOMONAS THAT ARE CAPABLE OF DEGRADING METHYL TERT-BUTYL ETHER (MTBE) INTO A SOLUTION IN EFFLUENT

This invention relates to microorganisms of the genus that are capable of degrading gasoline additives and in particular methyl tert-butyl ether (MTBE) or tert-butyl alcohol (TBA) into a solution in water. The microorganisms according to the invention find their application in the water treatment industry. This invention also has as its object a process for the treatment of aqueous effluent containing methyl tert-butyl ether (MTBE) and/or tert-butyl alcohol (TBA) using such bacteria.

The invention relates to the bacterium of the genus *Pseudoxanthomonas*, and in particular to the strain deposited on Jul. 12, 2012 at the Pasteur Institute (CNCM, 25 rue du Docteur Roux, F-75724 PARIS Cedex 15, France) under No. CNCM I-4657, under the Budapest treaty, which strain will be irrevocably and without restriction or condition released to the public upon issuance of a patent.

STATE OF THE ART

It is known that additives are added to gasolines to improve engine performance; this is the case of oxygenated additives or ether-fuels: the methyl tert-butyl ether (referred to hereinafter as MTBE) is one of the ethers that can be used as an oxygenated additive in unleaded gasolines for the purpose of increasing the octane number thereof as well as the ethyl tert-butyl ether (referred to hereinafter as ETBE), which has preferentially been used in France and in Europe for several years because of its qualification as a biofuel. These compounds can be added to gasolines at a rate of 22% (v/v).

The transport of hydrocarbons, by land or water, poses numerous accident risks. Transport via pipeline, which is generally considered safer than by truck, train or tanker, can nevertheless generate pollution. It was estimated in 2010 that the pipelines represent the most common (27%) source of spills. Ground pollution by hydrocarbons is also due to truck or train accidents during transport, accidents during the filling of service station tanks, leaks in storage tanks in service stations, or on industrial sites. In addition to these major sources of pollution by hydrocarbons, there is chronic pollution that occurs during the filling of vehicle tanks in service stations or with leaks in vehicle tanks. In these last two cases, this chronic discharging of a very small quantity into the ground water is also important.

Among the compounds of the gasolines, all do not have the same toxicity and/or biodegradability, and this will determine their future in the environment. Benzene, for example, which is one of the monoaromatic compounds of the gasolines, is a compound that is very toxic but easily degraded by aerobiosis. Among the native compounds of gasolines that are resistant to biodegradation, it is possible to cite 2,2,4-trimethylpentane (referred to hereinafter as isooctane) or cyclohexane, whose toxicity levels are slightly lower.

The literature relative to the biodegradation of the compounds of gasolines or alkanes by microorganisms is important, and numerous microorganisms with capacities for degradation of these compounds have been isolated. In contrast, a more limited number of microorganisms with capacities for degradation of MTBE or TBA, whose biodegradation is slower than that of the so-called "easily biodegradable" compounds, have been isolated.

Because of the growing use of additives such as MTBE in the formulations of gasolines or diesel fuel, it is therefore necessary to know the future of these compounds in the case of accidental spillage leading to pollution of the ground and subterranean waters or of the surface waters. This necessity is all the greater in the case of MTBE because this compound is very soluble in water (40 g·L$^{-1}$), and it is considered to be potentially toxic, and, except for any consideration of toxicity, its presence in water at very low concentrations makes the water unsuitable for consumption because of the taste that it imparts thereto.

One object of the invention is to propose new microorganisms that are capable of biodegrading MTBE and optionally TBA that can reach acquiferous layers in cases of pollution.

SUMMARY OF THE INVENTION

The applicant discovered, surprisingly enough, that the bacteria of the genus *Pseudoxanthomonas* and in particular the strain deposited on Jul. 12, 2012 at the Pasteur Institute (CNCM, 25 rue du Docteur Roux, F-75724 PARIS Cedex 15, France) under No. CNCM 1-4657 had significant capacities for biodegradation of MTBE and TBA.

DETAILED DESCRIPTION OF THE INVENTION

The applicant observed that when MTBE is provided to the bacterium of the genus *Pseudoxanthomonas*, and in particular to the strain deposited on Jul. 12, 2012 at the Pasteur Institute (CNCM, 25 rue du Docteur Roux, F-75724 PARIS Cedex 15, France) under No. CNCM 1-4657, the former has proven capable of degrading it by producing tert-butyl alcohol (TBA) as an intermediate compound of the biodegradation that is then totally consumed by this bacterium. This observation shows that the bacterium of the genus *Pseudoxanthomonas* has all of the degradation enzymes, making it possible to go as far as the mineralization and the production of biomass.

The bacteria according to the invention have been isolated from microcosms that come from different environments that have been obtained by enrichment on a minimum medium containing MTBE as a single carbon source. This protocol was carried out according to the specific microorganism enrichment techniques known to one skilled in the art, and it is a method making it possible to select the bacteria that are capable of degrading the MTBE.

The resulting bacterial strains are isolated after these specific enrichment stages on petri dishes containing the rich medium conventionally used by one skilled in the art (Tripticase/soy or TS medium) but after dilution of this medium to 1/10 relative to the concentration that is conventionally used. These bacteria were then identified based on their DNA No. 16S sequence and by comparison with the databases of bacteria DNA, and then they were tested for their capacities for degradation of MTBE.

This invention also relates to a process for treatment of effluent containing MTBE and optionally TBA, in which the effluent is brought into contact under aerobic conditions in the presence of at least one bacterium of the genus *Pseudoxanthomonas*, deposited on Jul. 12, 2012 at the Pasteur Institute (CNCM, 25 rue du Docteur Roux, F-75724 PARIS Cedex 15, France) under No. CNCM 1-4657. The use of these bacteria for continuous treatment of effluent polluted by MTBE can be carried out, for example, in a biofilter where the bacteria are fixed on a mineral or organic substrate, or else they can be added as an inoculum to sludges from a sewage treatment plant, or in any other system that is suitable for the treatment of water and soil (biobarrier).

According to an advantageous embodiment, the treatment process can use the bacteria according to the invention in combination with the bacteria that are described in the patent application FR 2 944 006 when the effluent contains a cocktail of hydrocarbon compounds such as octane, benzene, ethylbenzene, toluene, m-xylene, p-xylene, cyclohexanol, cyclohexane, and isooctane. dr

BRIEF DESCRIPTION OF THE DRAWING

FIG. 1—These aspects as well as other aspects of the invention will be clarified in the detailed description of particular embodiments of the invention, with reference being made to the drawing of FIG. 1, in which FIG. 1 shows the changes in the concentration of MTBE, of TBA in the culture medium, and of $CO_2$ formed as a function of the contact time with the bacterium of the genus *Pseudoxanthomonas* CNCM 1-4657.

EXAMPLES

Growth of the Bacterium of the Genus *Pseudoxanthomonas* CNCM 1-4657 On A Mineral Medium In the Presence of MTBE As A Single Carbon Source A preculture of the bacterium of the genus *Pseudoxanthomonas* CNCM 1-4657 is made: the strain *Pseudoxanthomonas* CNCM 1-4657 is inoculated on a saline mineral medium MM supplemented with MTBE at approximately 200 mg.1J$^{-1}$ as a source of carbon and energy.

The medium MM has the following composition:

| | |
|---|---|
| $KH_2PO_4$ | 1.4 g |
| $K_2HPO_4$ | 1.7 g |
| $NaNO_3$ | 1.5 g |
| $MgSO_4, 7H_2O$ | 0.5 g |
| $CaCl_2, 2H_2O$ | 0.04 g |
| $FeCl_3, 6H_2O$ | 0.012 g |
| Concentrated Solution of Vitamins | 1 mL |
| Concentrated Solution of Oligoelements | 1 mL |
| $H_2O$ | 1 L |

The concentrated solution of vitamins has the following composition for 1 liter of distilled water:

| | |
|---|---|
| Biotin | 200 mg |
| Riboflavin | 50 mg |
| Nicotinic Acid | 50 mg |
| Pantothenate | 50 mg |
| p-Aminobenzoic Acid | 50 mg |
| Folic Acid | 20 mg |
| Thiamine | 15 mg |
| Cyanocobalamin | 1.5 mg |

The concentrated solution of oligoelements has the following composition for 1 liter of distilled water:

| | |
|---|---|
| $CuSO_4, 5H_2O$ | 0.1 g |
| $MnSO_4, 2H_2O$ | 1 g |
| $ZnSO_4, 7H_2O$ | 1 g |
| $AlCl_3, 6H_2O$ | 0.4 g |
| $NiCl_2, 6H_2O$ | 0.25 g |
| $H_3BO_3$ | 0.1 g |
| $CoCl_2, 6H_2O$ | 1 g |
| $Na_2MoO_4, 2H_2O$ | 1 g |
| $Na_2WO_4, 2H_2O$ | 1 g |

After growth on the dishes, this culture on a solid medium is used for inoculating 150 mL of a saline mineral medium as described in the example (the colonies are scraped with a glucose and directly introduced into the culture medium as an inoculum) to which MTBE is added at a final concentration of approximately 300 mg·L$^{-1}$ in an Erlenmeyer flask with a 500-mL capacity, closed with a Teflon-coated plug so as to prevent any loss of MTBE during the growth. Sampling is done at time t=0 for a metering of MTBE at the beginning by gas phase chromatography analysis with a flame ionization detector (CPG/FID). The flask is then incubated at 30° C. in a rotary stirring mechanism. Sampling for the metering of the substrate and its optional degradation products is done at regular intervals. The production of $CO_2$ that is produced in the gaseous phase is also measured by sampling said gaseous phase through the septum with a gas-tight syringe by analysis of $CO_2$ by gas phase chromatography with a Katharometer-type detector (CPG/TCD).

The result of this experiment is presented in FIG. 1. As is seen in this FIG. 1, MTBE is partially degraded into TBA with low concentration. This compound is then itself re-consumed and used as a growth substrate.

It is possible to apply the protocol that is described above to different bacteria for evaluating their capacity to degrade MTBE and therefore makes it possible to select the bacteria that are capable of degrading MTBE.

The entire disclosures of all applications, patents and publications, cited herein and of corresponding French Application No. 12/02104, filed Jul. 25, 2012 are incorporated by reference herein.

The invention claimed is:

1. A process for treating an effluent that comprises methyl tert-butyl ether and optionally tert-butyl alcohol as a growth substrate in which said effluent is brought into contact, under aerobic conditions, with at least one bacterium of the genus *Pseudoxanthomonas* deposited on Jul. 12, 2012 at the Pasteur Institute (CNCM, 25 rue du Docteur Roux, F-75724 PARIS Cedex 15, France) under No. CNCM I-4657.

2. A process according to claim 1, in which the bacterium is fixed in a biofilter.

3. A process according to claim 2, in which the bacterium is fixed on a mineral or organic substrate.

4. A process according to claim 1, in which the effluent is brought into contact with a sewage treatment sludge in which a bacterium of the genus *Pseudoxanthomonas* deposited on Jul. 12, 2012 at the Pasteur Institute (CNCM, 25 rue du Docteur Roux, F-75724 PARIS Cedex 15, France) under No. CNCM I-4657 has been inoculated.

5. A process according to claim 1, in which the bacterium is fixed on a mineral substrate.

6. A process according to claim 1, in which the bacterium is fixed on an organic substrate.

7. A process according to claim 1, wherein the effluent comprises tert-butyl alcohol.

8. A process according to claim 1, wherein the effluent does not comprise tert-butyl alcohol.

* * * * *